United States Patent [19]

Fisk et al.

[11] Patent Number: 5,000,873

[45] Date of Patent: Mar. 19, 1991

[54] N-(HYDROPHOBE AROMATIC)PYRIDINIUM COMPOUNDS

[75] Inventors: Thomas E. Fisk; Christopher J. Tucker, both of Midland, Mich.

[73] Assignee: The Dow Chemical Company, Midland, Mich.

[21] Appl. No.: 361,619

[22] Filed: Jun. 5, 1989

Related U.S. Application Data

[60] Continuation of Ser. No. 30,184, Mar. 26, 1987, abandoned, which is a division of Ser. No. 569,099, Jan. 9, 1984, Pat. No. 4,672,118.

[51] Int. Cl.$^5$ .............................................. C23F 11/10
[52] U.S. Cl. .................................... 252/391; 252/392; 252/390; 252/8.555; 422/12; 422/16; 106/14.16
[58] Field of Search ..................... 252/8.555, 390, 391, 252/392; 422/12, 16; 106/14.16

[56] References Cited

U.S. PATENT DOCUMENTS

| | | | |
|---|---|---|---|
| 2,501,209 | 3/1950 | Craig ..................................... | 546/347 |
| 3,236,881 | 2/1966 | Distler et al. ......................... | 546/347 |
| 3,575,985 | 4/1971 | Ritchie et al. ......................... | 546/347 |
| 3,766,197 | 10/1973 | Redmore ............................. | 546/347 |
| 4,071,746 | 1/1978 | Quinlan . | |
| 4,100,099 | 7/1978 | Asperger et al. . | |
| 4,101,654 | 7/1978 | Redmore . | |
| 4,102,804 | 7/1978 | Clouse et al. . | |
| 4,150,233 | 4/1979 | Chadwick ........................... | 546/347 |
| 4,174,370 | 11/1979 | Oude Alink et al. . | |
| 4,250,042 | 2/1981 | Higgins ....................... | 252/8.551 X |
| 4,339,349 | 7/1982 | Martin et al. ..................... | 252/8.555 |
| 4,541,946 | 9/1985 | Jones et al. . | |

OTHER PUBLICATIONS

Nys et al., "Statistical Analysis of a Series of Partition Coefficients with Special Reference to the Predictability of Folding of Drug Molecules. The Introduction of Hydrophobic Fragmental Constants (f values)", *Chimie Therapeutique*, No. 5 (Sep.-Oct. 1973), pp. 521-535.

Nys et al., "The Concept of Hydrophobic Fragmental Constants (f-values) II, Extension of Its Applicability to the Calculation of Lipophilicites of Aromatic and Heteroaromatic Structures", *Eur. J. Med. Chem.—Chimica Therapeutica*, No. 4, (Jul.-Aug. 1974), pp. 361-375.

Leo et al., "Calculation of Hydrophobic Constant (Log P) from $\pi$ and f Constants", *J. Medicinal Chemistry*, vol. 18, No. 9 (Sep. 1975), pp. 865-868.

Martin, *Quantitative Drug Design*, Marcel Dokker, Inc., New York (?), Chapter 4 (part) "Calculation of the Physical Properties of Compounds", pp. 61-79.

Balaban et al., "Pyrylium Salts: Syntheses, Reactions and Physical Properties", *Advances in Heterocyclic Chemistry*, Supp. 2, Academic Press, New York, (1982), pp. 114-123.

Sammes et al., *J.C.S. Perkin I*, pp. 1373-1378 (1978).

*Chem. Abs.*, 57:3402C, (1962), Praill et al., "Pyrylium Salts and Related Compounds I. Reaction Between Olefins and Acylium Perchlorates".

*Primary Examiner*—Richard D. Lovering
*Assistant Examiner*—Valerie Fee
*Attorney, Agent, or Firm*—Ann K. Galbraith; Michael S. Jenkins

[57] ABSTRACT

Corrosion of metal surfaces in contact with an aqueous medium is inhibited by incorporating a N-(hydrophobe aromatic)pyridinium compound such as N-(p-dodecylphenyl-2,4,6-trimethylpyridinium sulfoacetate into the aqueous medium.

12 Claims, No Drawings

N-(HYDROPHOBE AROMATIC)PYRIDINIUM COMPOUNDS

CROSS-REFERENCE TO RELATED APPLICATION

This is a continuation of application Ser. No. 030,184, filed Mar. 26, 1987 now abandoned, which is a divisional of Ser. No. 569,099, filed Jan. 9, 1984, now U.S. Pat. No. 4,672,118.

BACKGROUND OF THE INVENTION

This invention relates to N-(hydrophobe aromatic)-pyridinium compounds and to processes for their preparation and for their use as cationic surfactants, demulsifiers, corrosion inhibitors in acid media.

Pyridinium compounds represented by the formula:

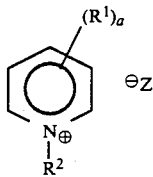

wherein $R^1$ is alkyl such as ethyl and methyl; $R^2$ is alkyl such as octyl and dodecyl, or aralkyl such as dodecylbenzyl; Z is an anion such as chloride and sulfate; and "a" is 0 or 1, are known to have surfactant activity in aqueous solutions. For example, such surfactants exhibit the following properties: adsorption at interfaces, micelle formation, solubilization of mixtures, reduction of surface and interfacial tension, wetting, foaming and antifoaming, emulsification, dispersion and aggregation, and detergency. These properties enable the surfactants to be used as fabric softeners, antistatic agents, anticoloring agents, herbicides, adhesion promoters, corrosion inhibitors, dispersants, toiletries, flotation aids and germicides.

Such compounds are prepared by reacting a substituted pyridine, e.g.,

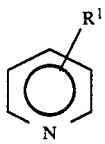

with an organic halide or sulfate, e.g., $Z\text{-}R^2$, wherein $R^1$, $R^2$ and Z are as defined before. Under conditions of elevated temperature, these compounds are susceptible to degradation. Thus, their use in the aforementioned applications at high temperatures is severely limited or not considered applicable.

Therefore, it would be highly desirable to provide surfactant compounds having good resistance to thermal degradation in addition to many of the desirable characteristics of conventional pyridinium surfactants.

SUMMARY OF THE INVENTION

In one aspect, the present invention is a N-(hydrophobe aromatic)pyridinium compound wherein the N-hydrophobe aromatic group has an aromatic moiety bonded to the nitrogen of the pyridinium ring and a hydrophobic moiety bonded to the aromatic moiety.

In another aspect, the present invention is a process for preparing N-(hydrophobe aromatic)pyridinium compounds which process comprises contacting a pyrylium salt with an aromatic amine under conditions sufficient to form the desired pyridinium compound.

In another aspect, this invention is a process for inhibiting corrosion of metal articles being contacted with an aqueous acidic medium which process comprises incorporating a N-(hydrophobe aromatic)pyridinium compound into the acidic medium prior to contacting the metal article.

Surprisingly, the N-(hydrophobe aromatic)-pyridinium compounds of this invention exhibit greater thermal stability than do N-aralkyl pyridinium compounds or N-alkyl pyridinium compounds. Thus, their desired surfactant properties are retained both during and after exposure to elevated temperatures. Therefore, such N-(hydrophobe aromatic)pyridinium compounds are useful in the aforementioned applications, particularly when the application involves exposure to such elevated temperatures. Such surfactants are also useful as counterions in the preparation of viscoelastic surfactants.

Even more surprising is the ability of these N-(hydrophobe aromatic)pyridinium compounds to provide better corrosion inhibition under a wider range of conditions than do N-aryl pyridinium compounds, N-aralkyl pyridinium compounds, or N-alkyl pyridinium compounds.

DETAILED DESCRIPTION OF THE ILLUSTRATIVE EMBODIMENTS

The N-hydrophobe aromatic pyridinium compounds of the present invention are compounds having a pyridinium ring and hydrophobe aromatic substituent bonded to the nitrogen of the pyridinium ring. The N-(hydrophobe aromatic)substituent comprises a hydrophobic group bonded to an aromatic moiety which is bonded to the nitrogen of the pyridinium ring. For the purposes of this invention, a hydrophobic group is one having a degree of hydrophobicity equal to or greater than propyloxy, preferably greater than hexyloxy, most preferably greater than octyloxy. Examples of such hydrophobe aromatic substituents include alkaryl, alkoxyaryl, polysiloxyaryl, perfluoroalkaryl, and polyalkyleneoxyaryl wherein alkylene is propylene or higher, with alkaryl being more preferred. Moreover, for the purpose of this invention, the term "alkaryl" includes aryl moieties having substituents in addition to the alkyl group.

In addition to the N-(hydrophobe aromatic)substituent, the pyridinium ring may also have other substituents such as alkyl, aryl, halo, carboxy, nitrile, haloalkyl, as well as heterocyclic and carbocyclic substituents which may be independent rings or rings fused with the pyridinium ring. The N-(hydrophobe aromatic)-pyridinium compound has any monovalent, divalent or trivalent anion as the counterion to the pyridinium cation. Examples of such anions include triflate, bisulfate, tetrafluoroborate, sulfoacetate, iodine, fluoride, bicarbonate, perchlorate, tetrachloroferrate, tetrachloroaluminate, methyl sulfate, formate, acetate, and others as listed hereinafter.

Preferred N-(hydrophobe aromatic)pyridinium compounds are represented by the formula:

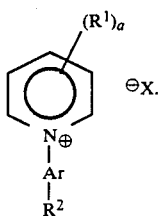

In the formula, each R[1] is independently alkyl, such as methyl, ethyl or propyl: haloalkyl, such as chloroethyl or bromomethyl; aryl, such as phenyl or naphthyl; haloaryl, such as chlorophenyl or bromophenyl; cycloalkyl or substituted cycloalkyl; nitrile, carboxy or carboxyalkylene, such as carboxymethylene or other monovalent organic moiety, particularly substituted forms of alkyl, aryl, alkoxy or aryloxy wherein the substituent is halo, alkyl, aryl, nitrile or alkoxy. Alternatively, two adjacent R[1] moieties are collectively alkylene or alkylene heteroalkylene to form a 5- or 6-membered carbocyclic or heterocyclic ring with the pyridinium ring such as butylene, propylene, ethyleneoxyethylene, ethyleneiminomethylene, or the like. Ar is a divalent aromatic moiety having at least one aromatic carbocyclic ring such as phenylene, biphenylene, naphthalenylene, diphenylene ether or similar moieties which may bear monovalent substituents such as alkoxy, alkyl, aryl/ halo, haloalkyl or the like in addition to R. Alternatively, Ar is a divalent heterocyclic aromatic moiety such as pyridinyl, pyrrolyl, furyl or similar moieties bearing one or more of the aforementioned monovalent substituents. R[2] is alkyl, alkoxy, perfluorohydrocarbyl, polysiloxy or other hydrophobic moiety having from 3 to 25 carbons. X is an anionic counterion such as halide, e.g., chloride, bromide, sulfoacetate, tetrafluoroborate, thiocyanate, bisulfate, toluenesulfonate, acetate, thiosulfate, salicylate, sulfate, and the like. The letter "a" represents an integer from 0 to 5. It is understood that a carbon of the pyridinium ring that is not bonded to one of the named substituents is bonded to hydrogen.

Most preferred N-(hydrophobe aromatic)pyridinium compounds are those wherein R[1] is phenyl or methyl; a is 3; Ar is phenylene; R[2,] which is positioned para or meta to the aromatic carbon bonded to the pyridinium ring, is octyl, decyl, dodecyl, tetradecyl, hexadecyl, octyloxy, decyloxy, dodecyloxy, tetradecyloxy, hexadecyloxy or octadecyloxy; and X is sulfoacetate, bisulfate or chloride. Examples of such most preferred compounds include N-(p--(n-dodecyl)phenyl)-2,4,6-trimethylpyridinium tetrafluoroborate; N-(p-octylphenyl)-2,4,6-trimethylpyridinium sulfoacetate or chloride; N-(p-(n-dodecyl)-phenyl)-2,4,6-triphenylpyridinium sulfoacetate or chloride; N-(p-(n-dodecylphenyl)-2,4,6-triphenylpyridinium bisulfate; N-(p-tetrapropylenephenyl)-2,4,6-trimethylpyridinium sulfoacetate, bisulfate or tetrafluoroborate; and the like.

The desired N-(hydrophobe aromatic)pyridinium compounds are prepared by reacting a pyrylium salt precursor, e.g., preferably a salt represented by the formula:

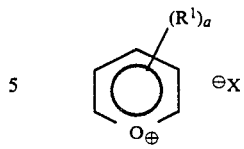

wherein R[1], X and a are as defined hereinbefore, with a primary amine having the desired hydrophobe aromatic substituent, e.g., preferably an amine represented by the formula:

$$H_2NAr-R^2$$

wherein Ar and R[2] are as defined hereinbefore. While the proportions of the salt and amine employed are not particularly critical, it is generally desirable to use them in approximately stoichiometric amounts. Preferably, the amount of amine employed is from about 0.9 to about 2 moles per mole of the pyrylium salt.

This process of preparation is advantageously carried out by contacting the pyrylium salt with the amine dissolved in a polar protic solvent, such as ethyl alcohol, or a polar aprotic solvent, such as methylene chloride, ethylene dichloride, or dimethylformamide, while mixing the reactants at a temperature sufficient to promote reaction. Preferably such temperature is in the range from about 0° C. to about 150° C., most preferably from about 30° C. to about 80° C. The reaction mixture is preferably maintained at this temperature for a period from about 1 to about 24 hours, most preferably from about 1 to about 6 hours. The desired N-(hydrophobe aromatic)pyridinium compound is readily recovered by conventional means such as removal of alcohol solvent by evaporation and washing with an ether or other suitable organic liquid that does not dissolve an appreciable amount of the compound.

The pyrylium salt precursor having alkyl substituents is advantageously prepared by the reaction of an olefin such as isobutene with acetic acid under acidic conditions, e.g., $H_2SO_4$ at 80° C., to produce the desired salt. When a pyrylium salt having aryl substituents is desired, an arylmethyl ketone, e.g., phenylmethyl ketone, is reacted with an arylethenyl aryl ketone, e.g., phenylethenyl phenyl ketone, in the presence of sulfuric acid at 95° C. to form the desired salt.

The N-(hydrophobe aromatic)pyridinium compounds are suitably employed as corrosion inhibitors by incorporating a corrosion-inhibiting amount of the compound in an aqueous acidic medium which is to contact the normally corrodible metal surface, e.g., steel or iron pipe or conduit or other metal part. Preferably, this amount is in the range from about 0.01 to about 10, more preferably from about 0.05 to about 5, most preferably from about 0.1 to about 4, weight percent based on the weight of the aqueous acidic medium. This method is most beneficially practiced at a temperature above 120° C., most preferably from about 150° C. to about 300° C.

It is understood that the acidic medium may contain other components or additives such as acids, surfactants, bleaches, thickening agents, and the like. Of particular interest in the practice of this aspect of this invention are the aqueous media that are employed in acidizing oil and gas wells. Such compounds are also useful as cationic surfactants in a wide variety of applications, particularly those which require that the surfactant have good thermal stability and good resistance to decomposition in the presence of acids. In such applications, the N-(hydrophobe aromatic) compound is advantageously employed in an amount in the range from about 0.001 to about 25 weight percent based on the weight of the aqueous medium being employed.

SPECIFIC EMBODIMENTS

The following examples are given to illustrate the invention and should not be construed as limiting its scope.

EXAMPLE 1

N-(p-octylphenyl)-2,4,6-trimethylpyridinium sulfoacetate

In a 500-ml round-bottom flask is placed 7.8 g (0.03 mole) of 2,4,6-trimethylpyrylium sulfoacetate. To this is added 300 ml of ethylene dichloride followed by 6.16 g (0.03 mole) of p-octylaniline.

This mixture is heated to reflux temperature with stirring for 3 hours. The ethylene dichloride is then removed with a rotary evaporator to yield a dark oil. This oil is washed with ether to give a light tan powder (12.0 g, 89 percent yield) of N-(p-octylphenyl)--2,4,6-trimethylpyridinium sulfoacetate as indicated by nuclear magnetic resonance ($^1$H) and elemental analysis.

EXAMPLE 2

N-(p-tetrapropylenephenyl)-2,4,6--trimethylpyridinium sulfoacetate

In a 500-ml round-bottom flask is placed 2.6 (0.01 mole) of 2,4,6-trimethylpyrylium sulfoacetate. To this is added about 300 ml of methylene chloride followed by 2.6 g (0.01 mole) of p-tetrapropyleneaniline. This mixture is heated to reflux with stirring for 3 hours. The methylene chloride is then removed with a rotary evaporator to give a viscous dark oil (4.9 g, 97 percent yield) of N-(p-tetrapropylenephenyl)-2,4,6-trimethylpyridinium sulfoacetate as indicated by nuclear magnetic resonance ($^1$H) and elemental analysis.

EXAMPLE 3

N-(p-tetrapropylenephenyl)-2,4,6-trimethylpyridinium tetrafluoroborate

Into a 500-ml flask is placed 6.3 g (0.01 mole) of 2,4,6-trimethylpyrylium tetrafluoroborate. To this is added 250 ml of ethylene dichloride followed by. 7.8 g of p-(n-tetrapropylene)aniline. This mixture is heated to reflux temperature, with stirring, for 3 hours. The ethylene dichloride is then removed with a rotary evaporator to give the dark waxy solid (14.0 g, 100 percent yield) of the aforementioned tetrafluoroborate as confirmed by nuclear magnetic resonance ($^1$H) and elemental analysis.

EXAMPLE 4

N-(p-tetrapropylenephenyl)-2,4,6--triphenylpyridinium bisulfate

In this synthesis, 6.1 g (0.015 mole) of 2,4,6-triphenylpyrylium bisulfate is placed in a 500-ml round-bottom flask and 150 ml of ethanol is added. To this 7.8 g (0.03 mole) of p-tetrapropyleneaniline is added and the mixture is heated at reflux temperature, with stirring, for 8 hours. The ethanol is then removed with a rotary evaporator to give a tan waxy solid (5.8 g, 60 percent yield) of N-(p-tetrapropylenephenyl)-2,4,6--triphenylpyridinium bisulfate as indicated by nuclear magnetic resonance ($^1$H) and elemental analysis.

EXAMPLE 5

N-(p-octylphenyl)-2,4,6-triphenylpyridinium triflate

A 4.58-g portion (0.01 mole) of 2,4,6-triphenylpyrylium triflate is added to 200 ml of ethanol. To this solution, 2.05 g (0.01 mole) of p-n-octylaniline is added. The mixture is refluxed for about 20 hours. Upon removing the ethanol by rotating evaporation, an orange oil remains. To remove the last of the ethanol the oil is placed under high vacuum.

The resulting product is frozen with liquid nitrogen and transferred to an ampule. The product is then washed with large amounts of cyclohexane and filtered. This gives 4.91 g (0.0076 mole) of a white powder which is determined to be N-(p-octylphenyl)-2,4,6---triphenylpyridinium triflate (yield 75 percent).

EXAMPLE 6

N-(p-dodecylphenyl)-2,4,6--triphenylpyridinium triflate

A 2.3-g portion (0.005 mole) of 2,4,6-triphenylpyrylium triflate is placed in a 500-ml round-bottom flask. To this, 200 ml of ethanol is added and then 1.3 g (0.005 mole) of p-dodecylaniline is added. The mixture is refluxed for about 20 hours. The ethanol is removed by evaporation to give a yellow waxy substance. This material is washed with ether which causes some yellow crystals to precipitate.

The ether is then removed to yield a dark green semi-liquid waxy material which is then washed with pentane. When the pentane is removed by filtration, a light green powder remains. The yield of N-(p-dodecylphenyl)-2,4,6-triphenylpyridinium triflate is 2.54 g (0.0036 mole) (yield 72 percent).

EXAMPLE 7

N-(p-decylphenyl)-2,4,6--triphenylpyridinium bisulfate

In a 500-ml round-bottom flask is placed 2.03 g (0.005 mole) of 2,4,6-triphenylpyrylium bisulfate. To this is added 150 ml of ethanol followed by 2.34 g (0.01 mole) of p-decylaniline. This mixture is refluxed for about 8 hours and allowed to cool. A quantity of the starting aniline precipitates and is removed by filtration. The ethanol is then removed to give a yellow waxy material which is washed with ether to give a white powder. This material is then dissolved in acetonitrile to cause the remaining aniline to precipitate. The acetonitrile is removed to give the desired product which is then rinsed with ether to remove any residual acetonitrile. The yield is 1.77 g (0.0028 mole) of 2,4,6-triphenylpyridinium bisulfate as confirmed by nuclear magnetic resonance ($^1$H) and elemental analysis.

EXAMPLE 8

N-(p-tetradecylphenyl)-2,4,6--triphenylpyridinium bisulfate

In a 500-ml round-bottom flask is placed 2.03 g (0.005 mole) of 2,4,6-triphenylpyrylium bisulfate. To this is added 150 ml of ethanol followed by 2.90 g (0.01 mole) of p-tetradecylaniline. This mixture is heated at 90° C. for about 8 hours and then allowed to cool. Upon cooling some of the starting aniline separates and is removed by filtration. The ethanol is then removed to give a yellow waxy substance which is rinsed with ether to remove any excess pyrylium. The resulting product is then dissolved in acetonitrile to remove any aniline still present. The acetonitrile is then stripped and the product is rinsed a final time with ether. The final product is a yellow crystal which turns a pale yellow color upon grinding. The yield is 0.71 g (0.00105 mole) of N-(p-tetradecylphenyl)--2,4,6-triphenylpyridinium bisulfate (yield 21 percent).

EXAMPLE 9

Several of the aforementioned N-(hydrophobe aromatic) compounds are tested for corrosion inhibition using the following test method and the results are reported in Table I.

Corrosion Test Method

Test samples (40 cm$^2$ area) of carbon steel (98.7 weight percent Fe, 0.3 weight percent Mn and 0.05 weight percent C) are (a) pickled for 10 minutes in 10 percent hydrochloric acid solution, (b) rinsed with water, (c) rinsed with acetone, (d) dried in air, and (e) weighed. The test samples thus prepared are then suspended from glass hooks and completely immersed in a stirred 15 weight percent hydrochloric acid solution for 18-24 hours. The test samples are (a) then removed from the acid solutions, (b) washed and scrubbed with warm water, (c) rinsed with acetone, (d) dried, and (e) reweighed. The weight loss resulting from such treatment is a measure of corrosion. Weight loss rate (WLR in lb/ft$^2$) is determined as follows:

$$WLR = \frac{(49.15)(WL)}{(OW)(SF)(t)}$$

wherein 49.15 is a conversion factor for converting gm/cm$^2$/hr to lb/ft$^2$/day, WL is weight loss in grams (g), OW is original weight in grams, SF is strip factor or average ratio of surface area (cm$^2$) to weight (g) and t is time in hours.

The quantity of acid solution in each case is about 2000 g. At least two steel samples are used and averaged for each solution. Inhibitor effectiveness is determined by comparing the WLR of an acid solution containing inhibitor against the WLR of a control solution which is identical except that it contains no inhibitor. The comparative data is reported as "Percent Protection" which is calculated as follows:

$$\frac{Percent}{Protection} = \frac{WLR(control) - WLR(inhibited)}{WLR(control)} \times 100$$

TABLE I

| Sample No. | Inhibitor[1] Type | Amount, % | Temp °C. | Time hr | WLR[2] lb/ft$^2$/day | % Protection[3] |
|---|---|---|---|---|---|---|
| 1 | A | 0.005 | 26.7 | 23.0 | 0.0168 | 88 |
| 2 | B | 0.005 | 26.7 | 23.0 | 0.0254 | 81 |
| 3 | C | 0.005 | 26.2 | 23.0 | 0.0339 | 75 |
| 4 | D | 0.005 | 28.0 | 24.0 | 0.0204 | 85 |
| 5 | E | 0.05 | 26.9 | 23.0 | 0.0051 | 96 |
| 6 | F | 0.05 | 26.4 | 23.0 | 0.0044 | 97 |
| 7 | G | 0.005 | 25.9 | 23.0 | 0.552 | 59 |
| C$_1$* | None | | 24.2 | 22.0 | 0.1362 | 0 |
| 8 | E | 0.05 | 65.0 | 4.5 | 0.4962 | 83 |
| 9 | H | 0.05 | 65.0 | 4.5 | 0.0892 | 97 |
| 10 | F | 0.05 | 65.0 | 5.7 | 0.1102 | 96 |
| 11 | I | 0.05 | 65.0 | 4.5 | 0.1530 | 95 |
| 12 | F | 0.1 | 65.0 | 24.0 | 0.0486 | 98 |
| 13 | E | 0.1 | 65.0 | 24.0 | 0.1734 | 94 |
| C$_2$* | None | | 65.0 | 2-4 | 2.860 | 0 |
| 14 | I | 0.005 | 28.4 | 23.0 | 0.0971 | 29 |
| 15 | I | 0.005 | 28.4 | 23.0 | 0.0311 | 77 |
| 16* | I | 0.000075 | 25.4 | 23.0 | 0.1297 | 5 |
| 17 | F | 0.2 | 65.0 | 24.0 | 0.0146 | 99.5 |

*Not an example of the invention.
[1]Type of inhibitor wherein:
A - Compound of Example 1
B - N-(p-decylphenyl)-2,4,6-trimethylpyridinium sulfoacetate
C - Compound of Example 2
D - Compound of Example 3
E - N-(p-(n-dodecyl)phenyl)-2,4,6-trimethylpyridinium sulfoacetate
F - N-(p-tetrapropylenephenyl)-2,4,6-trimethylpyridinium sulfoacetate
G - Compound of Example 4
H - N-(p-(n-dodecyl)phenyl)-2,4,6-trimethylpyridinium tetrafluoroborate
I - N-(p-(n-hexadecyl)phenyl)-2,4,6-trimethylpyridinium sulfoacetate
Amount of inhibitor as weight percent based on the weight of the acid solution.
[2]Weight Loss Rate as determined by the aforementioned Corrosion Test Method.
[3]Percent Protection as determined by the aforementioned Corrosion Test Method.

As evidenced by the data set forth in Table I, the N-(hydrophobe aromatic) compounds of the present invention exhibit substantial corrosion inhibition capability. Sample No. 16 is not considered to be an example of the invention because an insufficient amount of the inhibitor was added to the acid solution.

EXAMPLE 10

Stability of Alkaryl Pyridinium Surfactants

A 50-ml portion of a dilute (0.01 mole, 0.50 weight percent) solution of N-(p-dodecylphenyl)-2,4,6--trimethylpyridinium sulfoacetate is placed in a glass tube. This solution is then placed in a sealed pressure vessel and heated over a 3-hour period to 280° C. It is maintained at 280° C. for 3 hours and then allowed to cool to room temperature. The amount of alkaryl-2,4,6-trimethylpyridinium salt present in the sample is monitored by examination of a characteristic absorbance at 280 nm in the ultraviolet spectrum. No decomposition is observed.

Following the same procedure, N-(p-dodecylphenyl)-2,4,6-trimethylpyridinium chloride is tested for stability; again, no decomposition is observed.

A solution of N-(p-dodecylphenyl)2,4,6-trimethylpyridinium sulfoacetate is placed in a sealed glass ampule and heated to 200° C. for 2 weeks. The amount of alkaryl-2,4,6-trimethylpyridinium salt present before and after is again monitored by UV spectroscopy. No change (decomposition) is observed after this period.

What is claimed is:
1. A method of corrosion inhibition which comprises contacting a normally corrodible metal surface with an aqueous medium containing a N-(hydrophobe aromatic)pyridinium compound represented by the formula:

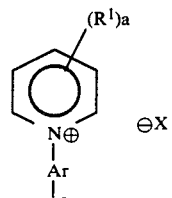

wherein each R$^1$ moiety is independently alkyl, alkoxy, aryl, aryloxy, halo, cycloalkyl, nitrile, carboxy or carboxyalkylene; or substituted forms of alkyl, aryl, aryloxy or alkoxy, wherein the substituent is halo, alkyl, aryl or alkoxy; or two adjacent $R^1$ moieties are collectively alkylene or alkylene heteroalkylene to form a 5- or 6-membered carbocyclic or heterocyclic ring with the pyridinium ring; Ar is a divalent aromatic moiety having at least one aromatic carbocyclic ring or at least one aromatic heterocyclic ring; $R^2$ is a hydrophobic moiety having a degree of hydrophobicity equal to or greater than a propyloxy moiety; X is an anionic counterion; and a is a number from 0 to 5; said pyridinium compound being present in an amount which is effective to inhibit the corrosion of the metal surface that normally occurs when the metal surface is contacted with an aqueous medium containing no corrosion inhibitor.

2. The method of claim 1 wherein $R^2$ is alkyl, alkoxy, perfluoroalkyl, polyalkyleneoxy, polysiloxy or other hydrophobic moiety having from 2 to 25 carbons.

3. The method of claim 2 wherein $R^2$ is alkaryl, alkoxyaryl, perfluoroalkylaryl, or polyalkyleneoxyaryl.

4. The method of claim 2 wherein $R^2$ is alkyl.

5. The method of claim 4 wherein $R^2$ is an alkyl moiety with at least three carbon atoms.

6. The method of claim 1 wherein $R^1$ is phenyl or methyl; a is 3; Ar is phenylene; $R^2$ is alkyl or alkoxy wherein alkyl is octyl, decyl, dodecyl, tetradecyl, hexadecyl, octadecyl or other alkyl having from 8 to 20 carbons; and X is sulfoacetate; tetrafluoroborate or bisulfate.

7. The method of claim 1 wherein the N--(hydrophobe aromatic)pyridinium compound is N-(p--dodecylphenyl)-2,4,6-trimethylpyridinium tetrafluoroborate.

8. The method of claim 1 wherein the N--(hydrophobe aromatic)pyridinium compound is N-(p--dodecylphenyl-2,4,6-triphenylpyridinium bisulfate.

9. The method of claim 1 wherein the N--(hydrophobe aromatic)pyridinium compound is N-(p--octylphenyl)-2,4,6-trimethylpyridinium sulfoacetate.

10. The method of claim 1 wherein the N--(hydrophobe aromatic)pyridinium compound is N-(p--dodecylphenyl)-2,4,6-trimethylpyridinium sulfoacetate.

11. The method of claim 1 wherein the effective amount of the N-(hydrophobe aromatic)pyridinium compound is from about 0.05 to about 5 weight percent based on the aqueous medium.

12. The method of claim 1 wherein the N--(hydrophobe aromatic)pyridinium compound is present in an amount of from about 0.01 weight percent to about 10 weight percent, based on the weight of the aqueous medium.

* * * * *